US00PP19239P3

(12) United States Plant Patent
van Kleinwee

(10) Patent No.: US PP19,239 P3
(45) Date of Patent: Sep. 16, 2008

(54) *BRACTEANTHA* PLANT NAMED 'HELISBRABIC'

(50) Latin Name: *Bracteantha bracteata*
Varietal Denomination: Helisbrabic

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/651,296

(22) Filed: Jan. 9, 2007

(65) Prior Publication Data

US 2008/0184424 P1 Jul. 31, 2008

(51) Int. Cl.
*A01H 5/00* (2006.01)

(52) U.S. Cl. ..... Plt./359

(58) Field of Classification Search ..... Plt./359
See application file for complete search history.

*Primary Examiner*—Kent L. Bell
*Assistant Examiner*—June Hwu
(74) *Attorney, Agent, or Firm*—S. Matthew Edwards

(57) ABSTRACT

A new *Bracteantha* plant particularly distinguished by its upright plant habit, good field performance, long narrow dark green colored leaves, freely flowering with numerous inflorescences per plant; and daisy-type inflorescences with semi-double pink flowers that are more pale towards inner whorls.

1 Drawing Sheet

Latin name of the genus and species of the plant claimed: *Bracteantha bracteata.*
Varietal denomination: 'Helisbrabic'.

BACKGROUND OF THE NEW PLANT

The present invention relates to a new distinct variety of Straw Daisy plant, botanically known as *Bracteantha bracteata* and hereinafter referred to by the variety name 'Helisbrabic.'

The new *Bracteantha* resulted from open-pollination of a proprietary selection of *Bracteantha bracteata* identified as 'B541-1' as the seed parent and a proprietary selection of *Bracteantha bracteata* identified as 'C3185-1' as the pollen parent. 'B541-1' has bigger flowers, bigger foliage, and a deeper pink color compared to the new *Bracteantha.* 'C3185-1' is less branching, is less floriferous, and has lighter green foliage compared to the new *Bracteantha.* Seed of this combination was harvested in 2002 and the new variety 'Helisbrabic' was selected in 2003 as one of the plants of this population. Breeder's code of the new plant is 'E0247-2.'

This new plant is an annual. The new variety is a product of a planned breeding program conducted in Enkhuizen, The Netherlands. The new cultivar 'Helisbrabic' is heat tolerant, compact, and flowers throughout the summer. 'Helisbrabic' is sexually reproduced by cuttings for 3 years now and trialled under different conditions in Europe. It has retained its distinctive characteristics through successive propagation and is firmly fixed. The new variety reproduces true to type in successive generations of asexual reproduction.

SUMMARY OF THE INVENTION

The new *Bracteantha* has not been observed under all possible environmental conditions. The phenotype may vary somewhat with variations in environment such as temperature and light intensity without, however, any variance in genotype.

The following characteristics have been repeatedly observed and are determined to be basic characteristics of 'Helisbrabic' and distinguish the new *Bracteantha* as a new and distinct variety:

1. Compact, upright plant habit
2. Freely branching habit and short internodes; dense and bushy plant habit
3. Early flowering
4. Freely flowering habit with number inflorescences per plant
5. Daisy-type inflorescences with approximately 5 whorls of pink flowers that are more pale towards inner whorls
6. Dark green with long and narrow foliage

TABLE 1

DIFFERENCES BETWEEN THE NEW VARIETY 'HELISBRABIC' AND TWO SIMILAR VARIETIES

| | 'Helisbrabic' | 'Sundaze Gold' (not patented) | 'Mohave Dark Rose' (not patented) |
|---|---|---|---|
| Plant height | 33 cm | 20 cm | 25 cm |
| Plant width | 28 cm | 50 cm | 45 cm |
| Number of whorls in flower | 5 | 7 | 14 |
| Leaf length | 5-13 cm | 4-11 cm | 5-13 cm |
| Leaf width | 1-2.5 cm | 1-2.5 cm | 1-2.5 cm |
| Flower color | 72A with base of 70D in outer whorls, 69D for inner whorls | 61A inner, 61C outer whorls | 61A inner and outer whorls |

DESCRIPTION OF THE DRAWING

This new *Bracteantha* plant is illustrated by the accompanying photographic drawing which shows blooms, buds and foliage of the plant in full color, the color shown being as true as can be reasonably obtained by conventional photographic procedures.

DESCRIPTION OF THE NEW VARIETY

The following detailed descriptions set forth the distinctive characteristics of this new *Bracteantha* plant. The data which defines these characteristics were collected from asexual reproductions carried out in Enkhuizen, Netherlands. The plant history was taken on 30 week old plants, grown in the open field in Enkhuizen, The Netherlands with day temperatures ranging from 16 to 30° Celsius, and night temperatures ranging from 10 to 16° Celsius.

Color references are primarily to the R.H.S. Colour Chart of The Royal Horticultural Society of London.

The plant:

*Classification.*—Botanical: *Bracteantha bracteata.*

Parentage:

*Female parent.*—Proprietary seedling *Bracteantha bracteata* 'B541-1,' not patented.

*Male parent.*—Proprietary seedling *Bracteantha bracteata* 'C3185-1,' not patented.

Propagation:

*Type cutting.*—Terminal vegetative cuttings.

*Time to initiated roots.*—7–10 days at air temperature of 21 degrees C.

*Time to develop roots.*—7–14 days at air temperature of 18 degrees C.

*Root description.*—Fibrous, relatively fine, white in color.

*Rooting description.*—Freely branching, dense.

Plant description:

*Growth habit.*—Upright and rounded shape.

*Plant height.*—33 cm.

*Vigor.*—Vigorous upright.

*Spreading area of plant.*—28 cm.

*Strength.*—Stems are very strong.

*Branching character.*—Freely branching, plants do not require pinching. Commonly develops approximately 14 lateral branches.

*Crop time.*—About 9 weeks are required to produce a finished flowering plant in a 10.5 cm container from a good developed cutting.

Lateral branch description:

*Length.*—Up to 40 cm.

*Diameter.*—Up to 9 mm.

*Shape.*—Round.

*Anthocyanin pigmentation.*—Absent.

*Texture.*—Hirsute, very lightly pubescent.

*Length of internode.*—6–44 mm.

*Color.*—Young branch 145B, old branch 146C.

The foliage:

*Arrangement.*—Alternate, simple.

*Shape of leaf.*—Lanceolate.

*Leaf.*—Apex: Broadly acute. Base: Attenuate.

*Margin.*—Entire.

*Length.*—5–13 cm.

*Width.*—1–2.5 cm.

*Color.*—Upper side: Old leaves: 137A, young leaves: 144B. Lower side: Old leaves: 137B, young leaves: 144A.

*Venation (on lower side).*—Pubescence: Midvein very lightly pubescent. Color: Old leaf: upper side 137B, base 146D, lower side lighter than 146D. Young leaf: upper and lower side lighter than 146D.

Inflorescence description:

*Appearance.*—Disc florets and involucre bracts develop acropetally on a capitulum. Inflorescences held upright and outwardly on terminal and axillary peduncles. Inflorescences positioned perpendicular to the peduncles.

*Flowering response.*—Under natural conditions, plant flower from Spring to early Fall in N-W Europe; plants flower freely continuous during this period.

Flower bud:

*Peduncle.*—Length : 0.5–11 cm. Diameter: 2 mm. Strength: Strong. Aspect: Erect. Texture: Slightly pubescent. Color: 146C.

*Inflorescence bud.*—Height: 2 cm. Diameter: 12 mm. Shape: Ovoid. Color: 158B at base to 72B at top.

Inflorescence:

*Size.*—Diameter: 4 cm. Depth: 1.6 cm.

*Diameter of disc.*—1.4 cm.

*Form.*—Double, composite, persistent inflorescences.

Involucre/phyllaries:

*Quantity.*—Approx. 43 involucre bracts in 5 whorls.

*Aspect.*—Flat.

*Appearance.*—Smooth, papery.

*Shape.*—Ligulate.

*Apex.*—Acute.

*Base.*—Truncate.

*Texture — Upper and lower.*—Smooth, glabrous.

*Margin.*—Entire.

*Length.*—Up to 18 mm.

*Width.*—Up to 6 mm.

*Color.*—Upper and lower side: color varies between 72A for outer whorls with base of 70D, to 69D for inner whorls.

*Fragrance.*—Absent.

Disc florets:

*Arrangement.*—Massed at the center of the inflorescence.

*Shape of disc florets.*—Tubular with approximately 22 hairs of 6 mm long (color closest to 155D).

*Color.*—Immature: Hairs 155C, top 16A. Mature: 17A.

*Disc floret.*—Diameter: 0.5 mm. Length: 7 mm.

*Quantity per inflorescence.*—Numerous, average 300.

Androecium:

*Pollen color.*—Yellow 23A.

Gynoecium:

*Stigma.*—Color: Yellow orange 32A. Shape: Bilobed.

Seed/fruit:

*Seed.*—Present. Length: 2 mm. Diameter: 1 mm. Shape: Tubular. Color: Lighter than 200D.

Disease resistance: Neither susceptibility nor resistance to fungal, bacterial or viral pathogens has been noted.

Temperature/weather tolerance: Plants of the new *Bracteantha* have been observed to be tolerant to rain, wind and to temperatures from 10° C. to 30° C.

What is claimed is:

1. A new and distinct variety of *Bracteantha* plant, substantially as illustrated and described herein.

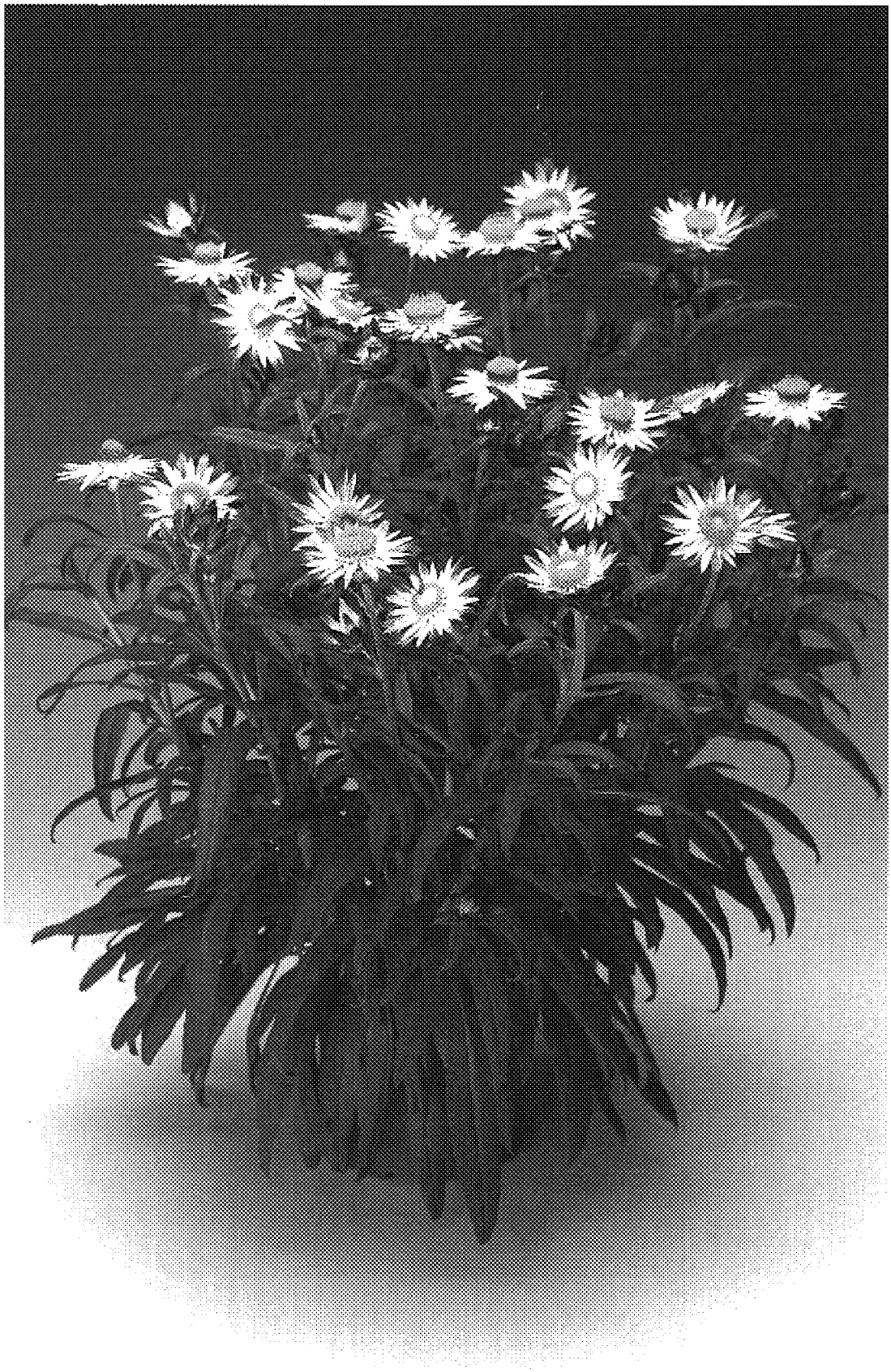

* * * * *